(12) United States Patent
Toshimitsu et al.

(10) Patent No.: US 9,707,188 B2
(45) Date of Patent: Jul. 18, 2017

(54) TRANSDERMAL PREPARATION

(75) Inventors: Arata Toshimitsu, Tsukuba (JP); Satoshi Amano, Tsukuba (JP); Kumi Morimoto, Tsukuba (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 650 days.

(21) Appl. No.: 13/580,168

(22) PCT Filed: Feb. 24, 2011

(86) PCT No.: PCT/JP2011/054154
§ 371 (c)(1),
(2), (4) Date: Aug. 21, 2012

(87) PCT Pub. No.: WO2011/105492
PCT Pub. Date: Sep. 1, 2011

(65) Prior Publication Data
US 2012/0315318 A1   Dec. 13, 2012

(30) Foreign Application Priority Data
Feb. 24, 2010 (JP) .............................. P2010-039319

(51) Int. Cl.
*A61F 13/02* (2006.01)
*A61K 9/70* (2006.01)
*A61K 9/00* (2006.01)

(52) U.S. Cl.
CPC .......... *A61K 9/7061* (2013.01); *A61K 9/0014* (2013.01); *A61K 9/0021* (2013.01)

(58) Field of Classification Search
CPC .. A61K 9/0012; A61K 9/0019; A61K 9/0014; A61K 9/0021; A61K 9/7023; A61K 9/7038; A61K 9/7061; A61K 9/7084

USPC .................................................. 424/448, 449
See application file for complete search history.

(56) References Cited

U.S. PATENT DOCUMENTS

| | | | |
|---|---|---|---|
| 8,580,281 B2 | 11/2013 | Morimoto et al. | |
| 2008/0317690 A1* | 12/2008 | Battaglia ......................... 424/60 |
| 2009/0099502 A1* | 4/2009 | Tokumoto et al. ............. 604/21 |
| 2011/0002976 A1* | 1/2011 | Yamamoto et al. . A61K 9/7061 424/448 |
| 2011/0008398 A1* | 1/2011 | Morimoto ............ A61K 9/7061 424/400 |
| 2011/0028880 A1* | 2/2011 | Uchida et al. .................. 602/48 |

FOREIGN PATENT DOCUMENTS

| | | |
|---|---|---|
| JP | 57-176908 A | 10/1982 |
| JP | 58-65168 A | 4/1983 |
| JP | 2007-16019 A | 1/2007 |
| JP | 2007-16020 A | 1/2007 |
| WO | 2005/102393 A1 | 11/2005 |
| WO | 2007/116959 A1 | 10/2007 |
| WO | 2007/126067 A1 | 11/2007 |

OTHER PUBLICATIONS

International Preliminary Report on Patentability for International Patent Application No. PCT/JP2011/054154; mailed on Sep. 27, 2012.

* cited by examiner

*Primary Examiner* — Micah-Paul Young
(74) *Attorney, Agent, or Firm* — Nath, Goldberg & Meyer; Joshua B. Goldberg; Tanya E. Harkins

(57) ABSTRACT

A transdermal preparation comprising a multivalent metal chloride, a basic drug having an amino group, and an ester group-containing base material, is useful because of its excellent drug content stability.

6 Claims, 5 Drawing Sheets

(a)

(b)

(c)

TRANSDERMAL PREPARATION

This is a National Phase Application filed under 35 U.S.C. §371 as a national stage of International Application No. PCT/JP2011/054154, filed on Feb. 24, 2011, claiming the benefit from Japanese Patent Application No. P2010-039319, filed on Feb. 24, 2010, the content of each of which is hereby incorporated by reference in its entirety.

TECHNICAL FIELD

The present invention relates to a transdermal preparation.

BACKGROUND ART

For a transdermal preparation, it is necessary to ensure not only transdermal absorption properties of a drug, but also the storage stability of a preparation. Consequently, various methods for inhibiting degradation of a drug and maintaining a drug stably in a preparation have been investigated.

Such methods include:
(1) if a drug unstable against light is contained, a method of adding a UV absorber in a preparation, or using a backing, a liner, or a packaging bag with light intercepting properties;
(2) if a drug is unstable against oxidation, a method of adding an antioxidant or enclosing an oxygen absorber in a package;
(3) if a drug is unstable against water, a method of selecting an oily preparation ingredient, or adding a water-absorbing ingredient in the preparation, or, according to need, enclosing a desiccant in a packaging bag; and
(4) if a drug is sensitive to acidic or basic conditions, a method of adding a pH regulator to regulate the drug to a pH at which a drug can exist stably. The methods can improve the stability of a drug by eliminating a factor for inducing degradation of the drug.

Meanwhile, the content of a drug may occasionally decrease due to a reaction between the drug and an ingredient present in a preparation. In this case, the most preferable method is to replace the ingredient easy to react with the drug with an ingredient difficult to react. But in this case, preparation performance, such as transdermal absorption properties and preparation physical properties (adhesiveness, skin irritation, etc.) may be changed remarkably, and therefore design of an appropriate formulation may become difficult.

A method of adding a metal chloride, such as magnesium chloride, calcium chloride, and zinc chloride, to a pressure sensitive adhesive has been disclosed (Patent Literatures 1 to 2) as a method for stabilizing migration properties of a drug to the skin.

Further, a transdermal absorption agent, in which a pressure-sensitive adhesive layer containing a predetermined drug, a metal chloride and a pressure-sensitive adhesive, and subjected to a crosslinking treatment, is formed on at least one side of a backing, has been disclosed, and according to the disclosure decrease in the cohesion force of the pressure-sensitive adhesive layer can be prevented (Patent Literature 3).

CITATION LIST

Patent Literature

Patent Literature 1: Japanese Patent Application Laid-Open No. 57-176908
Patent Literature 2: Japanese Patent Application Laid-Open No. 58-65168
Patent Literature 3: Japanese Patent Application Laid-Open No. 2007-16020

SUMMARY OF INVENTION

Technical Problem

However it has been difficult to enhance effectively the stability (content stability) of the drug content in a transdermal preparation (especially, the drug content of a transdermal preparation containing a basic drug having an amino group) by applying a known technology. Consequently, an object of the present invention is to provide a transdermal preparation superior in the content stability of a basic drug having an amino group. "Superior in the content stability of a drug" means to have high performance in maintaining a drug stably in a preparation.

Solution to Problem

The present invention provides a transdermal preparation comprising a multivalent metal chloride, a basic drug having an amino group, and an ester group-containing base material, wherein the transdermal preparation is laminated in a layer form on a backing and thereby formed in a patch shape. The transdermal preparation comprises multivalent metal chloride, a basic drug having an amino group, and an ester group-containing base material, and may be formed in a paste form, a cream form, a jelly form, a gel form, a milky liquid form or a liquid form.

By adopting the ingredients, the content stability of a basic drug having an amino group can become especially superior. According to the knowledge of the inventors, it is believed that a basic drug having an amino group and an ester group-containing base material can easily form a bond, but by adding a multivalent metal chloride, the basic drug having an amino group is coordinated with the multivalent metal chloride (which is believed to function as a Lewis acid), so as to lower the reactivity of the amino group and inhibit a chemical reaction with the base material having a functional group (an ester group) which reacts with an amino group from progressing. It is presumed that an improving effect on the drug content stability can be obtained as the result of the above.

Examples of a bond between a basic drug having an amino group and an ester group-containing base material include those based on reactions forming a covalent bond with a nitrogen atom, such as an addition reaction, or a substitution reaction, and as a consequence a compound from condensation of a base material ingredient and a drug is formed. In some cases, a product formed by a primary reaction may be transformed secondarily by an elimination reaction, an oxidation reaction, a reduction reaction, etc., or may react secondarily with another ingredient.

The transdermal preparation may have a constitution, in which the multivalent metal chloride and the basic drug having an amino group are dispersed or dissolved in the ester group-containing base material (first embodiment). With respect to a transdermal preparation according to the embodiment, not only the drug content stability is high, but also the skin permeability of the basic drug having an amino group is improved.

The transdermal preparation may adopt a constitution, in which a drug layer containing the multivalent metal chloride and the basic drug having an amino group is formed on a formed product composed of the ester group-containing base material (second embodiment). A typical example of the constitution is a microneedle device, in which the formed product is a microneedle. With respect to a transdermal preparation according to the embodiment, high skin permeability of the basic drug having an amino group in addition to the drug content stability can be obtained.

With respect to a transdermal preparation according to the first embodiment, the skin permeability of the basic drug having an amino group is significantly improved by controlling the pH of the transdermal preparation to 7 to 9. This is presumably because the basic drug having an amino group is ionized at low pH. The pH of a preparation having a nonaqueous base material (a preparation substantially not containing water) among transdermal preparations according to the first embodiment can be measured by measuring the pH of a test solution, which is prepared by immersing the preparation in distilled water. In this regard, "substantially not containing water" means that a transdermal preparation does not contain moisture beyond a moisture content which will be eventually reached by moisture absorption from the atmosphere. Typically, the moisture content of a transdermal preparation having a non-aqueous base material is 7% by mass or less based on the total amount of the transdermal preparation, more preferably 5% by mass or less, and especially preferably 3% by mass or less. The pH of a preparation having an aqueous base material (a preparation containing water) among transdermal preparations according to the first embodiment can be measured directly. By varying the content of a multivalent metal chloride in a transdermal preparation, the pH of the transdermal preparation can be controlled to 7 to 9. Further, the pH may be controlled by adding a basic substance or an acidic substance.

The effect of high drug content stability or high skin permeability of a basic drug having an amino group is especially remarkable, if the multivalent metal chloride is aluminum chloride, and especially favorable, if the content of the multivalent metal chloride is 0.05 to 5% by mass based on the total amount of the transdermal preparation.

The present invention provides an administration method of a transdermal preparation, by which a transdermal preparation containing a multivalent metal chloride, a basic drug having an amino group, and an ester group-containing base material, and having a form selected from the group consisting of a paste form, a cream form, a jelly form, a gel form, a milky liquid form and a liquid form, is applied to the skin.

The present invention also provides an administration method of a transdermal preparation, by which a transdermal preparation containing a multivalent metal chloride, a basic drug having an amino group, and an ester group-containing base material, and laminated in a layer form on a backing, thereby forming as a whole a patch shape, is applied to the skin.

The present invention further provides an administration method of a transdermal preparation, by which a transdermal preparation with a drug layer containing the multivalent metal chloride and basic drug having an amino group formed on a formed product composed of the ester group-containing base material, is applied to the skin. In this case, the administration method of a transdermal preparation may be carried out by selecting a microneedle as the formed product, and by pricking the skin therewith.

Advantageous Effects of Invention

According to the present invention, a transdermal preparation superior in the content stability of a basic drug having an amino group can be provided.

DESCRIPTION OF EMBODIMENTS

Figure 1:
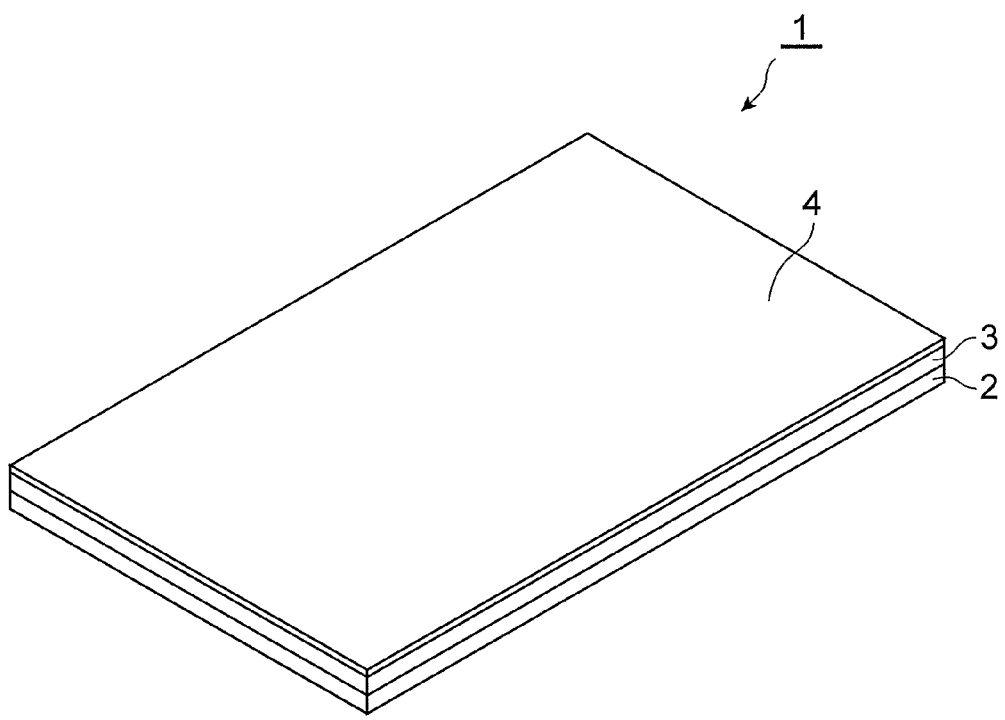
FIG. 1 is a perspective view showing an embodiment of a patch.

Embodiments of the present invention will be described below in detail, occasionally referring to the drawings. In this connection, in describing the drawings, identical or similar elements are provided with the same symbol and duplicated explanation will be omitted.

(Transdermal Preparation)

A transdermal preparation contains a multivalent metal chloride, a basic drug having an amino group, and an ester group-containing base material. A basic drug having an amino group means a drug being provided with an amino group and being basic, which is a drug having a tendency to react in the preparation with the ester group of a base material ingredient to form a compound condensed with the base material ingredient. Examples of an amino group include a primary or secondary amino group. In this connection, a secondary amino group means an imino group (—NH—). As an amino group, there are an aliphatic amino group and an aromatic amino group. The aliphatic amino group means an amino group having a C1 to C10, preferably C1 to C5 aliphatic substituent, which may have a substituent, including an alkyl group, an alkenyl group, and an alkynyl group. The aromatic amino group means an amino group having an aromatic substituent, which may have a substituent, including an aryl group, and a heteroaryl group. The amino group contained in a drug is preferably an aliphatic amino group, and more preferably an aliphatic secondary amino group. Compared to an aromatic amino group, an aliphatic amino group, especially an aliphatic secondary amino group has higher basicity and is easier to react with an ester group. Consequently, a basic drug having an aliphatic secondary amino group tends to exhibit significantly the improving effect on the drug content stability in a preparation.

A basic drug having an amino group may be a pharmacologically acceptable salt of the drug, and examples thereof include an acid salt of a basic drug, such as a hydrochloride, a nitrate, a succinate, a fumarate, a tartrate, a salicylate, a sulfate, a phosphate, and an acetate.

Specific examples of a drug include an antidementia drug (donepezil hydrochloride, etc.), a urination disorder improvement drug (tamsulosin hydrochloride, etc.), a sedative hypnotic agent (flurazepam hydrochloride, rilmazafone hydrochloride, etc.), an antipyretic antiphlogistic analgesic agent (butorphanol tartrate, perisoxal citrate, etc.), an analeptic stimulant (methamphetamine hydrochloride, methylphenidate hydrochloride, etc.), a psychoneurotic agent (chlorpromazine hydrochloride, imipramine hydrochloride, risperidone, aripiprazole, olanzapine, etc.), a local anesthetic (lidocaine hydrochloride, procaine hydrochloride, etc.), an agent affecting a urinary organ (oxybutynin hydrochloride, etc.), a skeletal muscle relaxant (tizanidine hydrochloride, eperisone hydrochloride, pridinol mesylate, etc.), an autonomic agent (carpronium chloride, neostigmine bromide, etc.), an antiparkinsonian agent (trihexyphenidyl hydrochloride, amantadine hydrochloride, pergolide mesylate, etc.), an antihistaminic agent (clemastine fumarate, diphenhydramine tannate, etc.), a bronchodilator (tulobuterol hydrochloride, procaterol hydrochloride, etc.), a cardiac (isoprenaline hydrochloride, dopamine hydrochloride, etc.), a coronary vasodilator (diltiazem hydrochloride, verapamil hydrochloride, etc.), a peripheral vasodilator (nicametate citrate, tolazoline hydrochloride, etc.), an aid to quitting smoking (varenicline tartrate, etc.), a cardiovascular agent (bisoprolol fumarate, flunarizine hydrochloride, nicardipine hydrochloride, etc.), an antiarrhythmic agent (propranolol hydrochloride, alprenolol hydrochloride, etc.), an antiallergic agent (ketotifen fumarate, azelastine hydrochloride, etc.), an anti-motion sickness agent (betahistine mesylate, difenidol hydrochloride, etc.), a serotonin receptor antagonist antiemetic agent, and a narcotic analgesic agent (morphine sulfate, fentanyl citrate, etc.).

The above drugs may be used singly, or in combinations of 2 or more, and include drugs in either of an inorganic salt form or an organic salt form. If the drug is applied as a patch, it is preferable to blend the same in a quantity of 1 to 50% by mass based on the total weight of the composition of a transdermal preparation in order to gain sufficient permeation quantity and to mitigate the skin irritation such as reddening.

A transdermal preparation contains in addition to the basic drug having an amino group a multivalent metal chloride, and the ingredient functions as a stabilizing agent for the drug.

As a multivalent metal chloride, a multivalent metal chloride of a bivalent or trivalent metal is preferable, and examples of such a chloride include magnesium chloride, calcium chloride, zinc chloride, stannous chloride, ferric chloride, and aluminum chloride, and aluminum chloride, whose metal is trivalent aluminum, is especially preferable.

Although there is no particular restriction on the addition quantity of a multivalent metal compound, insofar as the stabilizing effect (content stabilizing effect) of a drug can appear, normally it is added in the range of 0.05 to 5% by mass based on the total composition of a transdermal preparation. If the addition quantity is within the range, a stabilizing effect can be exerted without affecting seriously the preparation physical properties or the transdermal absorption properties. The range is more preferably 0.1 to 3% by mass, and further preferably 0.2 to 2% by mass.

A transdermal preparation contains, in addition to the basic drug having an amino group and the multivalent metal chloride as described above, an ester group-containing base material, and the ingredient functions as a carrier for the drug and the multivalent metal chloride.

Examples of the ester group-containing base material include polymers using a (meth)acrylic acid ester as a monomer unit. Such a polymer can be utilized effectively for the aforementioned first embodiment. Even for the first embodiment, if an application is carried out by means of a plaster (an embodiment of a patch), for an ester group-containing base material, a polymer (acrylic pressure-sensitive adhesive) exhibiting adhesiveness at an application temperature (room temperature to body temperature) is preferable.

As an acrylic pressure-sensitive adhesive, a polymer having polymerized a (meth)acrylic acid alkyl ester at a content of 40% by mass or higher is preferable. Especially preferable is a copolymer obtained by copolymerizing 50 to 98% by mass of a kind or 2 or more kinds of (meth)acrylic acid alkyl esters and 2 to 50% by mass of a kind or 2 or more kinds of copolymerizable monomers.

As such a (meth)acrylic acid alkyl ester, an ester obtained from a primary to tertiary alcohol with a C2 to C18, preferably C4 to C12 alkyl group, and acrylic acid or methacrylic acid can be used.

Meanwhile, as a copolymerizable monomer can be used a monomer having intramolecularly at least one unsaturated double bond participable in a copolymerization reaction, as well as in a side chain a functional group, such as a carboxyl group ((meth)acrylic acid, itaconic acid, maleic acid, maleic anhydride, etc.), a hydroxy group ((meth)acrylic acid hydroxyethyl ester, (meth)acrylic acid hydroxypropyl ester, etc.), a sulfoxyl group (styrenesulfonic acid, allylsulfonic acid, (meth)acrylic acid sulfopropyl ester, (meth)acryloyloxynaphthalenesulfonic acid, acrylamidemethylpropanesulfonic acid, etc.), an amino group ((meth)acrylic acid aminoethyl ester, (meth)acrylic acid dimethylaminoethyl ester, (meth)acrylic acid tert-butylaminoethyl ester, etc.), an amide group ((meth)acrylamide, dimethyl (meth)acrylamide, N-butyl acrylamide, N-methylol (meth)acrylamide, N-methylolpropane (meth)acrylamide, etc.), and an alkoxyl group ((meth)acrylic acid methoxyethyl ester, (meth)acrylic acid ethoxyethyl ester, (meth)acrylic acid methoxyethylene glycol ester, (meth)acrylic acid methoxydiethyleneglycol ester, (meth)acrylic acid methoxypolyethyleneglycol ester, (meth)acrylic acid methoxypolyethylene glycol ester, (meth) acrylic acid tetrahydrofurfuryl ester, etc.). Examples of a copolymerizable monomer to be used other than the above include (meth)acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam, vinyloxazole, and vinylmorpholine.

Although it is possible to copolymerize a kind or 2 or more kinds of the above copolymerizable monomers, from viewpoints of adhesion and cohesion as the adhesive properties, and the releasing properties of a basic drug and/or a pharmacologically acceptable salt thereof contained in a pressure-sensitive adhesive layer, it is preferable to copolymerize at least one kind of a monomer containing a carboxyl group or a monomer containing a hydroxy group in the range of 1 to 50% by mass, preferably 3 to 20% by mass, and to copolymerize, according to need, another monomer listed above, e.g., a vinyl monomer, such as vinyl acetate and N-vinyl-2-pyrrolidone in the range of 40% by mass or less, preferably 30% by mass or less.

Specific examples of an acrylic pressure-sensitive adhesive include a copolymer of 2-ethylhexylacrylate and acrylic acid, a copolymer of 2-ethylhexylacrylate and hydroxyethylacrylate, a copolymer of 2-ethylhexylacrylate and methylmethacrylate, a copolymer of 2-ethylhexylacrylate, 2-methoxyethylacrylate and vinyl acetate, a copolymer of 2-ethylhexylacrylate and vinylpyrrolidone, a copolymer of 2-ethylhexylacrylate, methylmethacrylate and 2-methoxyethylacrylate, and a copolymer of 2-ethylhexylacrylate, vinylpyrrolidone, and acrylic acid. Further, a commercial product may be used.

Further, to the above acrylic pressure-sensitive adhesive, to the extent that the storage stability of a drug is not decreased, a cross-linking agent, such as an epoxy compound, a polyisocyanate compound, a metal chelate compound, and a metal alkoxide compound, other than the above multifunctional monomers may be added. However, since the stabilizing effect of a multivalent metal chloride as a stabilizing agent can be sufficiently exerted according to the present invention, use of an acrylic pressure-sensitive adhesive to which a cross-linking agent is not added is preferable.

An acrylic pressure-sensitive adhesive may be used in combination with a pressure-sensitive adhesive, such as a natural rubber pressure-sensitive adhesive, a synthetic rubber pressure-sensitive adhesive (a synthetic isoprene rubber, a polyisobutylene rubber, a styrene/butadiene rubber, a styrene/isoprene/styrene rubber, and a styrene/butadiene/styrene rubber), a silicone pressure-sensitive adhesive, a vinyl ester pressure-sensitive adhesive, and a vinyl ether pressure-sensitive adhesive.

An acrylic pressure-sensitive adhesive may contain a liquid form ingredient compatible with a polymer constituting the pressure-sensitive adhesive. There is no particular restriction on such a liquid form ingredient, and an example thereof is a lipophilic liquid form ingredient, which may be an absorption enhancer, a solubilizer, a plasticizer, etc. Examples of an absorption enhancer include caprylic acid, caproic acid, lauric acid, myristic acid, palmitic acid, stearic acid, oleic acid, lauryl alcohol, myristyl alcohol, oleyl alcohol, stearyl alcohol, cetyl alcohol, methyl laurate, hexyl laurate, lauric acid dimethanolamide, and isopropyl myristate. Examples of a plasticizer include squalane, squalene, a silicon oil, a petroleum-derived oil (e.g., a paraffin process oil, a naphthene process oil, and an aromatic process oil), and a vegetable oil (e.g., an olive oil, a castor oil, a camellia oil, a tall oil, and a peanut oil). Examples of a solubilizer include dipropylene glycol, glycerol, ethylene glycol, and polyethylene glycol.

(Patch)

FIG. 1 is a perspective view showing an embodiment of a patch according to the aforementioned first embodiment of a transdermal preparation. A patch 1 shown in FIG. 1 is constituted of a sheet-formed backing 2 and a drug layer 3 laminated on a surface of the backing. On the surface of the drug layer 3 opposite to the backing 2, a release liner 4 is laminated. The patch 1 is used by peeling the release liner 4 and then sticking it, so as to make the drug layer 3 contact tightly with the skin of a patient, etc.

A patch can be produced by a process, such as a solvent process and a hot-melt process. If it is produced by a solvent process, ingredients including a multivalent metal chloride, a basic drug having an amino group, and an ester group-containing base material are dissolved or dispersed in a solvent, and the obtained dissolved solution or a dispersed solution can be spread over a backing, followed by removal of the solvent to form a drug layer, thereby obtaining a patch. If the blended ingredients can be applied by a hot-melt process, the ingredients are dissolved at a high temperature, and the obtained solution can be spread over a backing to form a drug layer, thereby obtaining a patch. On a surface of the drug layer opposite to the backing, a release liner may be further laminated.

In the above production processes, the dissolved solution or dispersed solution may be spread over a release liner instead of a backing for forming a drug layer, followed by laminating a backing together to obtain a patch.

Examples of a solvent to be used for production according to a solvent process include a lower alcohol, such as methanol, ethanol, and isopropanol, toluene, ethyl acetate, hexane, and cyclohexane.

As a backing layer a stretchable or non-stretchable backing may be used. For example, it may be selected out of a cloth, a nonwoven, polyurethane, polyester, polyvinyl acetate, polyvinylidene chloride, polyethylene, polyethylene terephthalate, an aluminium sheet, or a compound material thereof.

As a release liner, specifically a film of polyester such as polyethylene terephthalate, polyvinylchloride, polyvinylidene chloride, etc., a laminate film of woodfree paper and polyolefin, and the like can be used. Such a release liner is preferably subjected to a fluorine treatment or a silicon treatment at a surface of the release liner to be contacted with a pressure-sensitive adhesive layer so that the good workability in peeling the release liner from the adhering side can be improved.

If a transdermal preparation of the first embodiment is a cataplasm (an embodiment of a patch), examples of an ester group-containing base material include gelatin, CMC-Na (carboxymethylcellulose sodium salt), and a polyacrylic acid derivative, which may contain glycerol, propylene glycol, water, etc.

Examples of an embodiment other than a patch among transdermal preparations according to the first embodiment include those (an ointment, a cream, a gel, a liniment, a lotion, a tincture, etc.) prepared by dissolving or mixing and dispersing an ingredient containing a multivalent metal chloride and a basic drug having an amino group in an ester group-containing base material, and forming the same in a paste form, a cream form, a jelly form, a gel form, a milky liquid form, and a liquid form.

(Microneedle Device)

Examples of a transdermal preparation according to the second embodiment include a microneedle device. Examples of a microneedle device include a microneedle device provided with a substrate, a microneedle, which is provided on the substrate and is able to perforate the skin, and a drug layer, which is provided on the microneedle and/or the substrate, wherein the drug layer contains the aforementioned multivalent metal chloride and basic drug having an amino group, and the microneedle and/or the substrate is composed of an ester group-containing base material.

Figure 2:
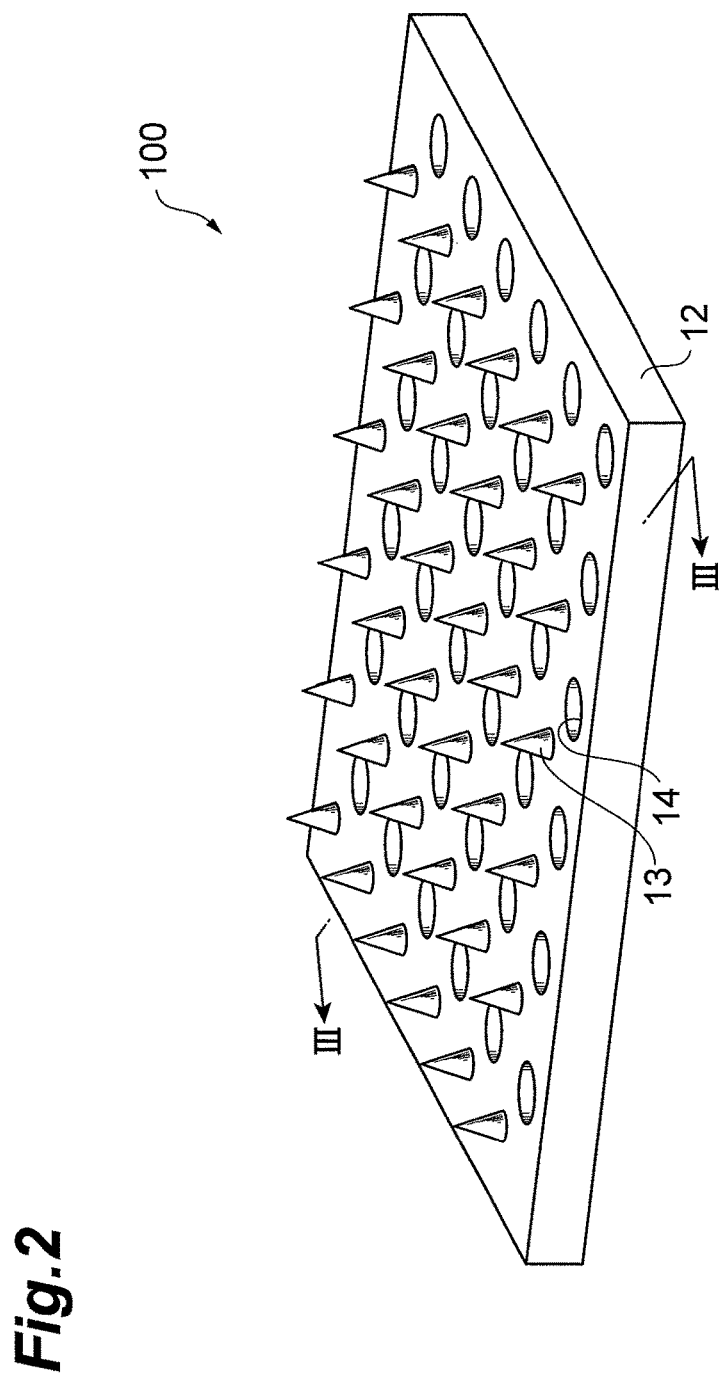
FIG. 2 is a perspective view showing an embodiment of a microneedle device.
Figure 3:
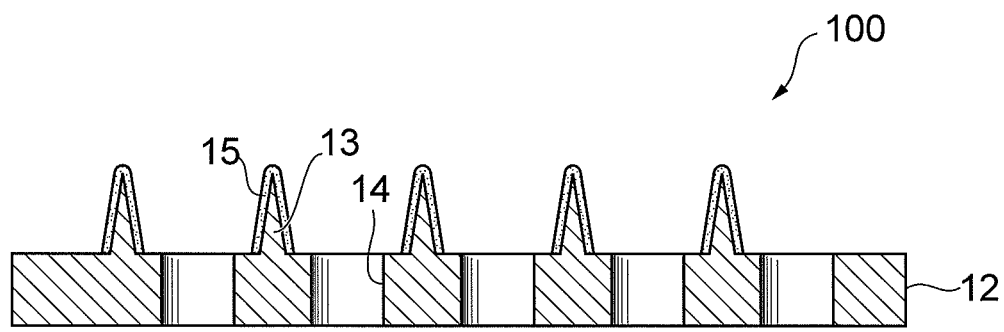
FIG. 3 is a cross-sectional view along the line III-III in FIG. 2.

FIG. 2 is a perspective view showing an embodiment of a microneedle device. FIG. 3 is a cross-sectional view along the line III-III in FIG. 2.

As shown in FIG. 2 a microneedle device 100 is provided with a microneedle substrate 12 and a plurality of microneedles 13, which are arranged two-dimensionally on the microneedle substrate 12 and able to perforate the skin.

The microneedle substrate 12 is a foundation for supporting the microneedles 13. In the microneedle substrate 12 are formed a plurality of through-holes 14 arranged two-dimensionally. The microneedles 13 and the through-holes 14 are arranged alternately in the diagonal direction of the microneedle substrate 12. By virtue of the through-holes 14, a drug can be administrated from the backside of the microneedle substrate 12. A substrate without a through-hole 14 may be also used. The area of the microneedle substrate 12 is 0.5 to 10 $cm^2$, preferably 1 to 5 $cm^2$, and more preferably 1 to 3 $cm^2$. By combining several microneedle substrates 12, a substrate with a desired dimension may be constituted.

The microneedle 13 has a miniature structure, whose height (length) H is preferably 50 to 500 µm. In this regard, the length of the microneedle 13 is set at 50 µm or more in order to secure a transdermal administration of a drug, and at 500 µm or less to decrease surely a risk of pain by preventing a microneedle from touching a nerve, as well as to avoid surely a risk of hemorrhage. Further, if the length of the microneedle 13 is 500 µm or less, a drug in an amount to be applied intracutaneously can be administered efficiently. The length of the microneedle 13 is preferably 300 to 500 µm, and especially preferably 400 to 500 µm.

A microneedle is not limited to a needle shape with a sharply pointed tip, and a shape without a pointed tip is allowable insofar as it has a convex structure. If the microneedle 13 has a conical structure, the diameter at the base is approximately 50 to 200 µm. Although in the current embodiment the microneedle 13 is conical, it may have a polyhedral (such as tetrahedral) pyramid shape. If it has a shape without a pointed tip, the area of a flat surface at the tip of a microneedle is preferably 20 to 600 µm² and more preferably 50 to 250 µm².

The microneedles 13 are typically provided at intervals forming a needle row such that a density of about 1 to 10 needles per mm is provided. In general, adjacent rows are apart by substantially the same distance from each other to the space of a needle in the rows, and the needle density is 100 to 10,000 needles per cm². If the needle density is 100 or higher, the skin can be perforated efficiently. Meanwhile, if the needle density exceeds 10,000, it becomes difficult to give the microneedle 13 enough strength to perforate the skin. The density of the microneedles 13 is preferably 200 to 5,000 needles per cm², further preferably 300 to 2,000 needles, and most preferably 400 to 850 needles.

As shown in FIG. 3, a drug layer 15 containing a multivalent metal chloride, and a basic drug having an amino group is formed on the microneedle 13.

Examples of an administration method for a drug using the microneedle device 100 include, but not limited to, a direct administration by hand pressing, an administration method, by which the microneedle device 100 is collided against the stratum corneum layer by an assistive device such as an applicator, and an administration method, by which a hand pressing administration is carried out using an assistive device.

When an ester group-containing base material is formed into microneedles or a microneedle array, a natural resin material may be an example for the base material. However, considering the antigenicity of a microspike as well as the material cost, a synthetic or natural resin material including a biodegradable polymer, such as polylactic acid, polyglycolide, polylactic acid-co-polyglycolide, and a non-degradable polymer, such as polycarbonate, and ethylene vinyl acetate, is especially preferable. Further, chondroitin sulfuric acid and a cellulose derivative, which are polysaccharides, are also suitable.

Examples of a method for producing the microneedle substrate 12 or the microneedle 13 include precision machining (electro-discharge machining, laser machining, dicing, hot embossing, injection molding, etc.), and cutting machining. By such a processing method, the microneedle substrate 12 and the microneedle 13 are formed integrally. After the production of the microneedle 13, it may be subjected to secondary processing by laser machining, etc. to make the microneedle 13 hollow.

Figure 4:
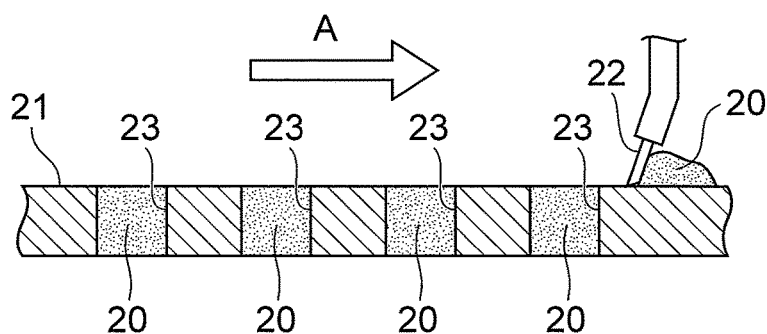
FIGS. 4(a) to (c) are diagrams showing an example of a process for producing a microneedle device.
Figure 4:
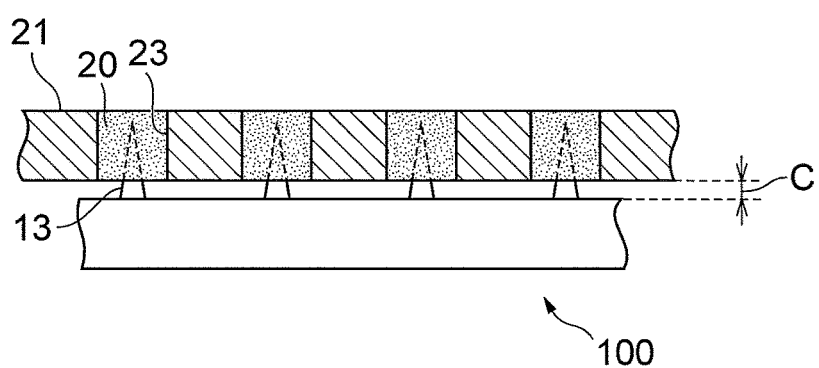
Figure 4:
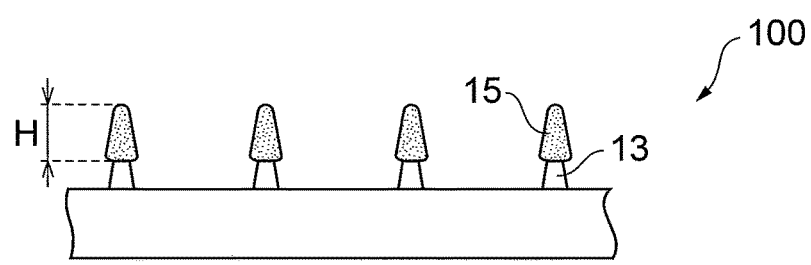

FIGS. 4(a) to (c) are diagrams showing an example of a method for forming the drug layer 15 on the microneedle 13. According to the method, as shown in FIG. 4(a), a drug composition 20 containing a multivalent metal chloride, and a basic drug having an amino group is firstly swept by a spatula 22 in the direction of the arrow A on a mask plate 21 to fill the drug composition 20 into openings 23. Then, as shown in FIG. 4(b), the microneedles 13 are inserted into the openings 23 of the mask plate 21. Thereafter as shown in FIG. 4(c), the microneedles 13 are drawn out of the openings 23 of the mask plate 21. Thereby, the drug layer 15 is formed on the microneedles 13. Then, the drug layer 15 on the microneedle 13 is dried by a heretofore known method, such as air drying, vacuum drying, freeze-drying or a combination thereof. Thereby, the drug composition 20 is fixed on the microneedles 13 as the drug layer 15.

The thickness of the drug layer 15 on the microneedle 13 is less than 50 µm, preferably less than 25 µm, and further preferably 1 to 10 µm. The thickness of the drug layer 15 means an average thickness measured after drying. The thickness of the drug layer 15 can be increased by repeating further the application of the drug composition 20 on a fixed drug layer.

When the drug layer 15 is formed on the microneedle 13, it is preferable to control the temperature and humidity constant for minimizing a change in the concentration of the agent and changes in the physical properties due to solvent volatilization of the drug composition 20. For preventing the solvent evaporation, it is preferable either to lower the temperature, or to increase the humidity, or to do both. If the temperature is not controlled, the humidity at room temperature is, as relative humidity, 50 to 100% RH and preferably 70.0 to 99.9% RH. If it is 50% RH or less, evaporation of a solvent occurs, and changes in the physical properties of the drug composition 20 may take place. Although as a humidification method, a vaporization method, a steaming method, a water spraying method, etc. are possible, any method may be employed insofar as an intended humidity condition can be realized.

EXAMPLES

The present invention will be described more specifically below referring to Examples, provided that the present invention be not limited to the Examples, and various changes can be made in it without departing from the technological spirit of the present invention. In Examples, "%" means always "% by mass".

(Stability of Preparation)

A produced patch was cut into a dimension of 10 cm² to obtain a sample to be used for a test. Each sample was packed hermetically in an aluminum packaging material and stored in a thermo-hygrostat at the temperature of 60° C. and the humidity of 75% for 2 weeks or 1 month, thereafter the remaining basic drug in each patch was extracted according to the following method, and the residual ratio with respect to each initial content was calculated as a relative value to the initial value (%).

(Measurement of Basic Drug Content in Patch)

After a release liner was peeled off from a patch, the drug was extracted by an organic solvent, and the content of the drug in the extract solution was analyzed by high performance liquid chromatography, to determine the content of the basic drug contained in each patch.

Values of the content of the basic drug ($N_i$) obtained by measuring each sample stored in a thermo-hygrostat with the temperature of 60° C. and the humidity of 75% for 2 weeks or 1 month, and the content of the basic drug ($N_0$) obtained by measuring the initial sample were substituted in the relation represented by the following formula (1) for calculation to obtain a value ($R_i$), which represents the quantity of the basic drug relative to the initial value (%) in each sample after storage under each condition.

$$R_i(\%) = N_f/N_0 \times 100 \quad (1)$$

(Skin Penetration Test)

The ventral part skin of a hairless mouse was peeled and mounted on a flow through cell circulated with 37° C.-warm water around the circumference, with the dermis side facing the receptor solution. Then, a patch with the application area of 5 cm² was applied on the stratum corneum layer side of the skin, and, using PBS for the receptor solution, the receptor solution was sampled at intervals of 2 hours for 24 hours. The flow rate was measured, and also the drug concentration was measured by high performance liquid chromatography, and using the measured values drug permeation rates per hour were calculated to determine the maximum value thereof (Jmax) μg/cm²/hr.

Comparative Example 1

Preparation Containing Bisoprolol (Production of Patch)

According to the formulation ratios shown in the following table, bisoprolol, which is a drug having an aliphatic secondary amino group, was added to a solution of an acrylate copolymer (acrylic pressure-sensitive adhesive) (type containing a —COOH group; solvent: ethyl acetate, toluene), and the mixture was stirred thoroughly to obtain a coating solution. Then, the obtained coating solution was coated on a release liner made of polyethylene terephthalate, and thereafter the solvents of toluene and ethyl acetate were removed by drying to form a layer containing the drug having a predetermined paste thickness (200 μm). Further, the layer containing the drug was laminated with a backing made of polyethylene terephthalate to obtain a patch according to Comparative Example 1.

TABLE 1

|  | Comparative Example 1 |
| --- | --- |
| Acrylate copolymer (Type containing —COOH group) | 60% |
| Bisoprolol | 40% |

(Evaluation of Drug Content Stability)

With respect to the patch of Comparative Example 1, the drug content was measured according to the aforementioned method, and the content stability was investigated. The results are as follows.

Bisoprolol content after 2 weeks, at 60° C.: 97.5%
Bisoprolol content after 1 month, at 60° C.: 94.9%

With respect to Comparative Example 1, there was almost no degradation product, which was presumed to be derived from bisoprolol, in an extract sample of the drug. Meanwhile, as the result of a precise analysis of a residue in the preparation after extraction of the drug, it was indicated that there existed a reaction product between the acrylate copolymer solution (type containing a —COOH group) and bisoprolol (by NMR a peak attributable to a hydrogen atom of a phenyl group of bisoprolol was identified). From the above, it was presumed that condensation between the drug and the ester group-containing base material took place.

Example 1, Comparative Examples 2 to 4

Preparations Containing Varenicline (Production of Patch)

According to the formulation ratios shown in, the following table, varenicline tartrate as a drug having an aliphatic secondary amino group and sodium hydroxide were stirred in a proper amount of methanol to obtain the mixture. Then the remaining ingredients were added to the acrylate copolymer (acrylic pressure-sensitive adhesive) (type containing an —OH group) and mixed to prepare a mixture, which was then added to the mixture obtained previously, followed by stirring thoroughly to obtain a coating solution. Then, the obtained coating solution was coated on a release liner made of polyethylene terephthalate, and thereafter the solvent was removed by drying to form a layer containing the drug having a predetermined paste thickness (100 μm). Further, the layer containing the drug was laminated with a backing made of polyethylene terephthalate to obtain a patch.

TABLE 2

|  | Example 1 | Comparative Example 2 | Comparative Example 3 | Comparative Example 4 |
| --- | --- | --- | --- | --- |
| Varenicline tartrate | 5.0 | 5.0 | 5.0 | 5.0 |
| Acrylate copolymer (Type containing —OH group) | 91.9 | 93.9 | 90.9 | 90.9 |
| Sodium hydroxide | 1.1 | 1.1 | 1.1 | 1.1 |
| Aluminum chloride | 2.0 | — | — | — |
| Sodium stearate | — | — | 3.0 | — |
| Zinc stearate | — | — | — | 3.0 |

(Evaluation of Drug Content Stability)

The temporal stability of varenicline preparations (Example 1, Comparative Examples 2 to 4) was evaluated according to the aforementioned method. The results are shown in the following table. In the table, for example, "60° C.-2 W" means storage conditions: at 60° C. for 2 weeks, and "60° C.-1 M" means: at 60° C. for 1 month (the same holds hereinbelow).

TABLE 3

|  | Drug content (%) | |
| --- | --- | --- |
|  | 60° C.-2 W | 60° C.-1 M |
| Example 1 | 97.82 | 97.2 |
| Comparative Example 2 | 96.2 | 92.9 |
| Comparative Example 3 | 95.3 | 90.4 |
| Comparative Example 4 | 94.2 | 90.3 |

Examples 2 to 7, Comparative Example 5

Preparation Containing Tamsulosin (Production of Patch)

The materials were mixed according to the formulation ratios shown in the following table. Tamsulosin hydrochloride as a drug having an aliphatic secondary amino group, sodium acetate, a fatty acid ester, and polyvinylpyrrolidone were mixed well in advance in a solvent, and then mixed with an acrylic polymer (acrylate copolymer (type containing an —OH group)) having dissolved aluminum chloride. After coated on a release liner, the solvent was removed by drying, and the liner was laminated with a polyethylene terephthalate film backing to obtain a patch.

As obvious from the results of Examples 1 to 6, Comparative Examples 1 to 5, with respect to a transdermal preparation having a pressure-sensitive adhesive layer containing a basic drug having an amino group and an acrylic pressure-sensitive adhesive, the drug content stability was improved by adding aluminum chloride.

TABLE 4

|  | Tamsulosin hydrochloride | Sodium acetate | Acrylate copolymer (Type containing —OH group) | Polyvinylpyrrolidone | Fatty acid ester | Aluminum chloride | pH of preparation |
|---|---|---|---|---|---|---|---|
| Comparative Example 5 | 5.0% | 1.4% | 83.6% | 5.0% | 5.0% | — | 8.49 |
| Example 2 |  |  | 83.5% | 5.0% | 5.0% | 0.1% | — |
| Example 3 |  |  | 83.4% | 5.0% | 5.0% | 0.2% | — |
| Example 4 |  |  | 83.3% | 5.0% | 5.0% | 0.3% | — |
| Example 5 |  |  | 83.2% | 5.0% | 5.0% | 0.4% | — |
| Example 6 |  |  | 83.1% | 5.0% | 5.0% | 0.5% | 7.97 |
| Example 7 |  |  | 82.6% | 5.0% | 5.0% | 1.0% | 4.84 |

(Evaluation of Drug Content Stability)

The temporal stability of preparations containing tamsulosin (Examples 2 to 6, Comparative Example 5) was evaluated according to the aforementioned method. The results are shown in the following table.

(Method for Measuring pH)

A preparation (5 cm$^2$), from which a release liner was peeled off, was immersed in 20 mL of distilled water, and stirred for 24 hours to obtain a test solution, the pH of which was then measured.

TABLE 5

|  | Drug content (%) | | | |
|---|---|---|---|---|
|  | 60° C.-2 W | 60° C.-1 M | 40° C.-1 M | 40° C.-3 M |
| Comparative Example 5 | 94.8 | 91.5 | 97.2 | 95.3 |
| Example 2 | 96.9 | 95.4 | 100.2 | 96.4 |
| Example 3 | 97.4 | 97.0 | 100.1 | 97.1 |
| Example 4 | 99.0 | 95.4 | 99.3 | 95.3 |
| Example 5 | 97.6 | 97.1 | 99.2 | 97.3 |
| Example 6 | 99.2 | 97.2 | 100.1 | 97.1 |

(Evaluation of Skin Permeability)

Figure 5:
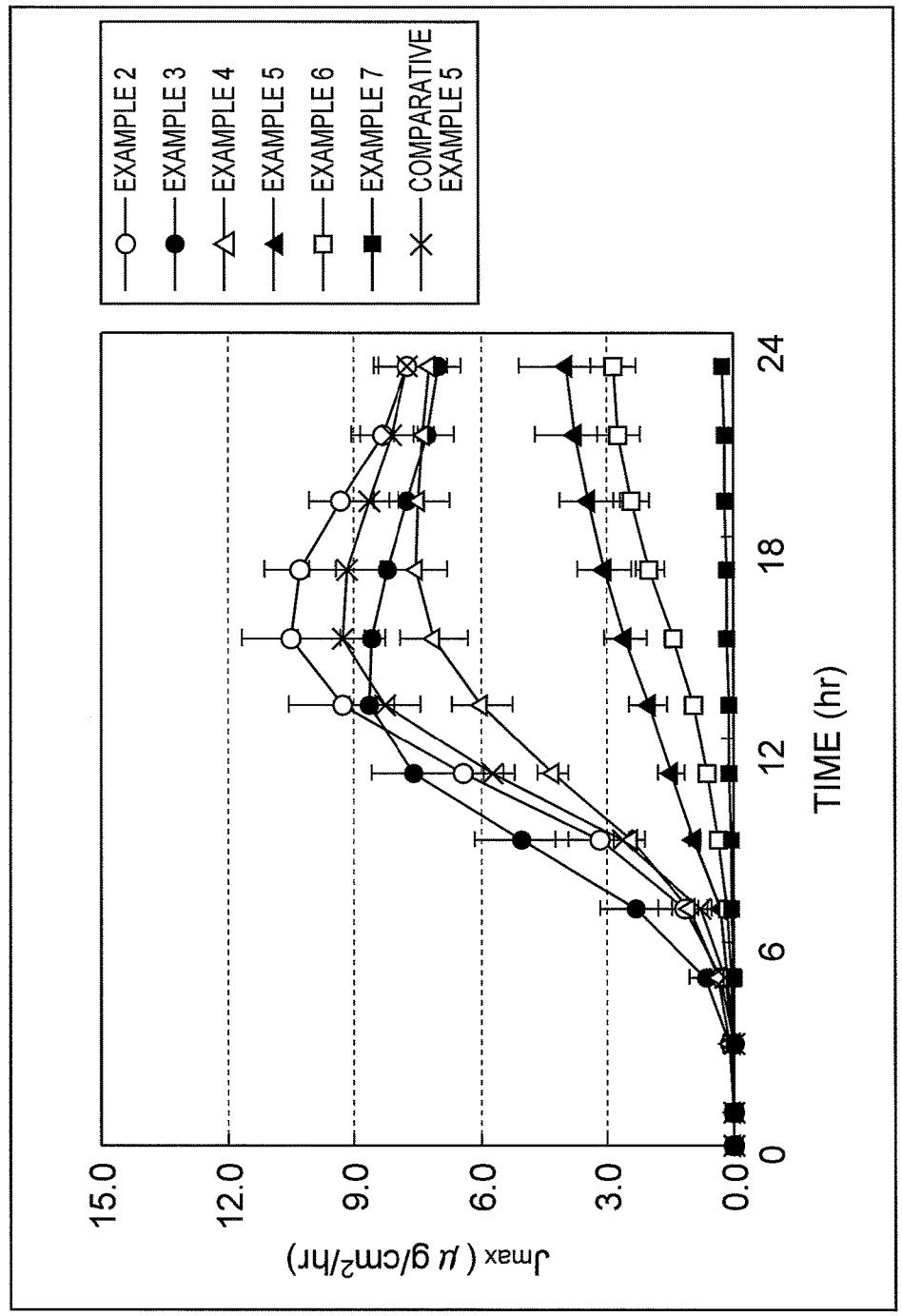
FIG. 5 is a graph representing the drug transdermal absorption properties of patches according to Examples 2 to 7 and Comparative Example 5.

Skin permeation tests of a drug with respect to preparations containing tamsulosin (Examples 2 to 7, Comparative Example 5) were conducted according to the aforementioned method. The results are shown in FIG. 5.

(Evaluation of Temporal Stability of Skin Permeability)

The temporal stability of skin permeability of a drug with respect to preparations containing tamsulosin (Example 3 and Comparative Example 5) was evaluated according to the aforementioned method. The results are shown in the following table.

TABLE 6

|  | Cumulative permeated amount after 24 hours (µg/cm$^2$) | | | | |
|---|---|---|---|---|---|
|  | Initial | 60° C.-2 W | 60° C.-1 M | 40° C.-1 M | 40° C.-3 M |
| Comparative Example 5 | 121.13 | 106.51 | 116.61 | 124.31 | 111.70 |
| Example 3 | 126.53 | 122.81 | 101.72 | 134.02 | 97.49 |

The results of the skin permeability tests about the preparations of Examples 2 to 7 shown in FIG. 5 show that the preparations with the pH of 7 or higher were also superior in the skin permeability. Further, from the results of the study on the temporal stability of the skin permeability, it was made clear that addition of 0.2% of aluminum chloride to a preparation containing tamsulosin having an aliphatic secondary amino group had little adverse effect on the temporal stability of the skin permeability.

As described above, by containing a multivalent metal chloride (especially aluminum chloride) in a preparation, the temporal stability of a basic drug was improved significantly. Although the reason why a multivalent metal chloride is effective is not clear, it is presumed that it would inhibit a reaction between a basic drug and a copolymer of a (meth)acrylic acid ester.

Grounds therefor include knowledge of the inventors, namely, an analysis was carried out, when a temporal bisoprolol content decrease was recognized with respect to a pressure-sensitive adhesive layer prepared by blending bisoprolol as a basic drug in an acrylic pressure-sensitive adhesive, to have confirmed that a reaction between bisoprolol and an acrylic copolymer had occurred indeed.

Not only for bisoprolol, but also for tamsulosin and varenicline, which have a basic amino group, the content decrease in a pressure-sensitive adhesive containing an acrylic acid ester copolymer was recognized, and there was almost no degradation product, which was presumed to be derived from tamsulosin or varenicline, in an extract solution of a pressure-sensitive adhesive layer. Therefore, it was believed to be highly possible, that as in the case of bisoprolol a reaction with the polymer (an ester group-containing base material) occurred.

INDUSTRIAL APPLICABILITY

According to the present invention, a transdermal preparation containing a variety of basic drugs and with high temporal content stability can be provided.

REFERENCE SIGNS LIST

1 . . . Patch, 2 . . . backing, 3, 15 . . . Drug layer, 4 . . . Release liner, 12 . . . Microneedle substrate, 13 . . .

Microneedle, 14 ... Through-hole, 20 ... Drug composition, 21 ... Mask plate, 22 ... Spatula, 23 ... Opening, 100 ... Microneedle device

The invention claimed is:

1. A transdermal preparation comprising: 0.05% to 5% aluminum chloride by mass based on the total amount of the transdermal preparation, varenicline tartrate, and an acrylic pressure-sensitive adhesive; wherein the transdermal preparation is laminated in a layer form on a backing and thereby formed in a patch shape.

2. A transdermal preparation comprising: 0.05% to 5% aluminum chloride by mass based on the total amount of the transdermal preparation, varenicline tartrate, and an acrylic pressure-sensitive adhesive; wherein the transdermal preparation is formed in a form selected from the group consisting of a paste form, a cream form, a jelly form, a gel form, a milky liquid form and a liquid form.

3. The transdermal preparation according to claim 1, wherein the aluminum chloride and the varenicline tartrate are dispersed or dissolved in the acrylic pressure-sensitive adhesive.

4. A transdermal preparation comprising: 0.05% to 5% aluminum chloride by mass based on the total amount of the transdermal preparation, varenicline tartrate, and an acrylic pressure-sensitive adhesive; wherein a drug layer containing the aluminum chloride and the varenicline tartrate is formed on a formed product composed of the acrylic pressure-sensitive adhesive.

5. The transdermal preparation according to claim 4, wherein the formed product is a microneedle.

6. The transdermal preparation according to claim 2, wherein the aluminum chloride and the varenicline tartrate are dispersed or dissolved in the acrylic pressure-sensitive adhesive.

* * * * *